United States Patent [19]

Inoue et al.

[11] Patent Number: 4,782,025

[45] Date of Patent: Nov. 1, 1988

[54] NOVEL MICROORGANISM

[75] Inventors: Shigeo Inoue; Yoshiharu Kimura, both of Utsunomiya, Japan

[73] Assignee: Kao Corporation, Tokyo, Japan

[21] Appl. No.: 755,092

[22] Filed: Jul. 15, 1985

[30] Foreign Application Priority Data

Jul. 25, 1984 [JP] Japan .................................. 59-154437

[51] Int. Cl.⁴ ............................................... C12N 1/16
[52] U.S. Cl. .................................... 435/255; 435/100; 435/171; 435/944
[58] Field of Search ................. 435/255, 100, 171, 944

[56] References Cited

PUBLICATIONS

Spencer et al. "Torulopsis bombicola sp. n.", Antonie van Leeuwenhoek 36, pp. 129–133, 1970.
Ito, et al. "Growth of Yeasts on n-Alkanes: Inhibition by a Lactonic Sophorolipid Produced by *Torulopsis bombicola*" *Agric. Biol. Chem.*, vol. 44, pp. 2221–2223, 1980.
Walker et al. "Formation of Gentiobiose, Sophorose and Other Oligosaccharides by *Acetobacter* Species Growing in Glucose Media", *Arch. Biochem. Biophys.*, vol. 83, pp. 161–169, 1959.

*Primary Examiner*—Charles F. Warren
*Assistant Examiner*—Irene Marx
*Attorney, Agent, or Firm*—Oblon, Fisher, Spivak, McClelland & Maier

[57]  ABSTRACT

A novel microorganism *Torulopsis bombicola* KSM-36 (FERM BP-799) isolated from cabbage leaves grown in a cabbage field located in Musashino-shi, Tokyo, has sophorose-producing activity.

1 Claim, 1 Drawing Sheet

FIGURE
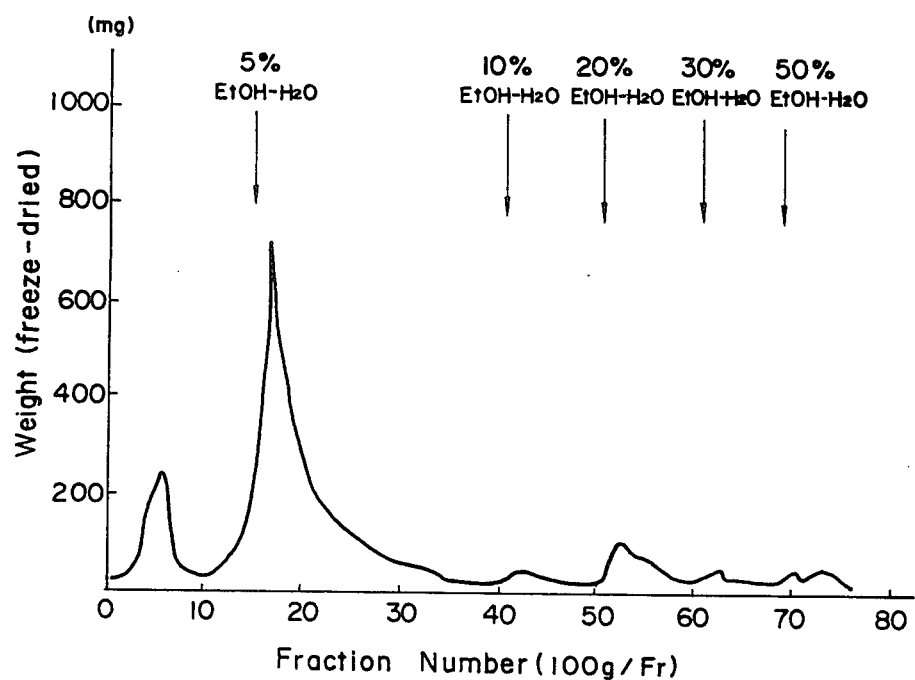

NOVEL MICROORGANISM

BACKGROUND OF THE INVENTION (i) Field of the Invention

This invention relates to a novel microorganism belonging to the genus Torulopsis.

(ii) Description of the Prior Art

Sophorose, which is useful as a substance capable of promoting the production of cellulase by bacteria and also as a raw material for cosmetics, was found out for the first time as the sugar component of the camphelol glycoside contained in the shells of fruits of *Sophora japonica* L. However, it is seldom obtained as a free disaccharide in the natural world. It is only known that sophorose is contained as a free disaccharide in royal jelly.

On the other hand, no production of sophorose by bacteria has yet been known except that Khan et al observed the formation of sophorose in small amounts in the course of their investigations on the formation of oligo-saccharides by microorganisms belonging to genus of bacterial Acetobacter [A. W. Khan et al, Nature, 183, 682(1959); T. K. Walker et al., Arch. Biochem. Biophys., 83, 161(1959)].

Under the above-mentioned present circumstances, it has been desired to find out sophorose-producing microorganisms urgently.

SUMMARY OF THE INVENTION

The present inventors made an extensive investigation with a view to discovering a microorganism having sophorose-producing capacity. As a result, it has been found that among microorganisms belonging to the genus yeast Torulopsis, there is a microorganism having such capacity, leading to completion of this invention.

Namely, this invention provides novel *Torulopsis bombicola* KSM-36 (FRI Deposition FERM BP-799) which belongs to the genus Torulopsis and has sophorose-producing capacity.

BRIEF DESCRIPTION OF THE DRAWING

The sole FIGURE is an elution curve showing the results of column chromatography in Referential Example 1.

DETAILED DESCRIPTION OF THE INVENTION AND PREFERRED EMBODIMENTS

*Torulopsis bombicola* KSM-36 has the following mycological properties:

(a) State of growth on various culture media:

Grown into elliptical to elongated elliptical yeasts having a size of (0.75 to 3.0)×(1.5 to 5.5) μm on malt culture medium, malt agar, potato dextrose agar, and corn meal agar, and no formation of euhyphae or pseudohyphae was observed by the multipolar budding type (b) Formation of ascospores:

Using malt extract agar, it was investigated whether ascospores were formed or not. As a result, no formation of ascospores was observed.

(c) Formation of ballistospores:

Cultured on malt agar to investigate whether ballistospores were formed or not. As a result, no formation of ballistospores was observed.

(d) Various physiological properties:

(1) Growth conditions:

pH: 3 to 8 (optimum pH: 5 to 6)
Temperature: 7 to 38° C.
(optimum temperature: 25 to 34° C.)

| | | |
|---|---|---|
| (2) | Assimilation of salts of nitric acid: | (−) |
| (3) | Decomposition of fat: | (+) |
| (4) | Decomposition of urea: | (−) |
| (5) | Liquefaction of gelatin: | (−) |
| (6) | Resistance to sodium chloride: | 6 to 8% (w/v) |
| (7) | Formation of carotenoid: | (−) |
| (8) | Formation of organic acids in Caster's culture medium: | (+) |
| (9) | Formation of starch-like substances: | (−) |
| (10) | Vitamin requirement: | (+) |

(e) Assimilating capacity and Fermenting capacity:

| | | Assimilating capacity | Fermenting capacity |
|---|---|---|---|
| (1) | D-glucose | (+) | (+) |
| (2) | Trehalose | (−) | (−) |
| (3) | D-Galactose | (−) | (−) |
| (4) | Lactose | (−) | (−) |
| (5) | Sucrose | (+) | (+) |
| (6) | Raffinose | (−) | (+½) |
| (7) | D-Mannose | (−) | (−) |
| (8) | D-Xylose | (−) | |
| (9) | α-Methyl-D-glucoside | (−) | |
| (10) | Melibiose | (−) | |
| (11) | D-Arabinose | (−) | |
| (12) | Esculin | (−) | |
| (13) | Ethanol | (+) | |
| (14) | Inositol | (−) | |
| (15) | Maltose | (−) | (−) |
| (16) | Melezitose | (−) | |
| (17) | Glycerin | (+) | |
| (18) | Cellobiose | (−) | |
| (19) | Inulin | (−) | |
| (20) | D-Mannitol | (+) | |
| (21) | Soluble starch | (−) | |
| (22) | D-Sorbitol | (+) | |

Note:
"+" means the property was observed, "−" means the property was not observed, a blank means the experiment was not carried out, and "+½" means the property was observed to be ½ the level of "+"

(f) Place of collection:

Isolated from cabbage leaves in a cabbage field located in Musashino-shi, Tokyo.

From the above mycological properties, the KSM-36 strain has been determined to belong to the genus Torulopsis. The above strain has the following additional features. Namely, no formation of skins was observed when the above strain was cultured in malt culture medium, YM culture medium and glucose-yeast extract-peptone culture medium respectively. It showed good growth on YM agar culture medium, and the resultant colony had such a shape that it arose along the entire peripheral edge thereof and was semi-lenticular. Its surface was smooth, it had a coruscant gloss, it showed buttery properties, and its tone was a cream color. When cultured into a macrocolony, the shape of the resultant colony was circular but its appearance and shape were similar to those of the colony cultured on YM agar culture medium.

With respect to microorganisms having such mycological properties, a research was made on the basis of J. Lodder, "The Yeasts", North-Holland Publishing Co., Amsterdam-London, 1971; Kazuo Komagata, "BISEIBUTSU NO KAGAKUBUNRUI JIKKENHO", Gakkai Center, 1982; and Hiroshi Iizuka and Shoji Goto, "KOBO NO BUNRUI DOTEIHO", 2nd ed., Tokyo Daigaku Shuppan Kai, 1977. As a result, it was found that *Torulopsis bombicola* ATCC 22214 (GBS6009) is a strain similar to the strain of the present invention. However, *Torulopsis bombicola* KSM-36 of this invention is a strain isolated from cabbage leaves by means of an isolating culture medium which contained n-alkanes as a sole carbon source substrate whereas the known *Torulopsis bombicola* yeast strain is a strain isolated from the flower honey of a wild flower (for example, the wild poppy in the province of Alberta, Canada) by means of an isolating culture medium which contained glucose at a high concentration as a sole carbon source substrate. *Torulopsis bombicola* KSM-36 of this invention is also different from the known *Torulopsis bombicola* yeast strain in that the former strain can assimilate urea, in other words, its urease activity is "+" while the urease activity of the latter strain is "−". Furthermore, as the most distinct difference, it may be mentioned that *Torulopsis bombicola* KSM-36 has far higher sophorose-producing capacity compared with the known *Torulopsis bombicola* yeast strain.

Accordingly, the present inventors determined KSM-36 strain as a novel yeast belonging to the genus *Torulopsis*, and named it *Torulopsis bombicola* KSM-36 and as mentioned above, deposited it with Fermentation Research Institute, Agency of Industrial Science and Technology 1-3, Higashi 1-chome, Tsukaba-shi, Ibaragi-ken 305, Japan.

In order to isolate this KSM-36 strain from cabbage leaves as its origin, it is only necessary to follow routine procedures while using a culture medium containing normal paraffin as a sole carbon source as mentioned above.

In order to produce sophorose using the KSM-36 strain of this invention, it is necessary to culture the KSM-36 strain in a culture medium containing a carbon source, nitrogen source or organic nutrient source, inorganic salt and the like which are required to permit good growth of the KSM-36 strain and smooth production of sophorose.

Any carbon sources may be employed as carbon sources so long as they can be assimilated, including carbohydrates (for example, glucose, fructose, sucrose, sorbitol, etc.), organic acids (for example, citric acid, succinic acid, etc.), hydrocarbons (for example, n-dodecane, n-hexadecane, etc.), oils and fats and their derivatives (for example, animal and vegetable oils, animal and vegetable fats, diglycerides, monoglycerides, fatty acids, fatty acid esters, aliphatic alcohols and their esters, etc.), alkyl (or alkenyl) halides, and so on. As nitrogen sources or organic nutrient sources, may for example be mentioned inorganic nitrogen source compounds such as ammonium sulfate, ammonium phosphate and ammonium nitrate; amino acids such as glutamic acid; organic nitrogen source substances such as yeast extracts, meat extracts and peptone, and the like. On the other hand, various phosphoric acid salts, magnesium sulfate and the like may be employed as inorganic salts. Besides, heavy metal salts are also used in trace amounts. Their addition may not be required for culture media which contain natural substances. Thiamine and biotin are required as vitamins. Their addition may not be required for culture media which contain natural substances. Furthermore, when its variants which require certain nutrients are used, substances satisfying such nutrient requirements must be added to culture media.

Its culture may be effected by sterilizing a culture medium by its heating or the like, inoculating it to the culture medium and then shaking or aeration-stirring the culture medium at 20° to 35° C. for 3 to 5 days. Regarding the pH, good results may be obtained when its initial pH is adjusted to 5 to 6.5 and the pH is thereafter left up to the culture. When a carbon source soluble hardly in water or a similar carbon source is used, it may be effective to add one or more of various surfactants, such as polyoxyethylenesorbitan, to culture media.

The thus-cultured mixture may be employed as a yeast source as it is. However, it may also be possible to separate the microorganism from the cultured mixture using usual solid-liquid separation means and then to provide the resultant live microorganism or its treated or processed product (lyophilized microorganism or the like) as a yeast source.

In addition, the isolation of sophorose from the cultured mixture may be carried out, as will be described later in Referential Examples, by collection and purification methods for general organic compounds, while making use of certain physical and chemical properties of sophorose.

Namely, the cultured mixture may for example be subjected to centrifugation, filtration, phase separation or the like to collect a culture liquid. After removing impurities from the culture liquid by such technique as extraction or ion exchange, sophorose is isolated and purified by column chromatography, which makes use of an activated carbon column or the like, or by a similar technique.

*Torulopsis bombicola* KSM-36 of this invention produces sophorose as will be described later in Referential Examples.

As described above, only one report has been known as to the sophorose-producing capacity of microorganisms. Moreover, the report merely discloses the formation of sophorose in small amounts. Contrary to the report, *Torulopsis bombicola* KSM-36 of this invention has extremely high sophorose-producing capacity.

This invention will hereinafter be described by the following Example and Referential Example.

EXAMPLE 1

(i) Ten grams of cabbage leaves obtained from a cabbage field at the outskirts of Musashino-shi, Tokyo were placed in a beaker which contained 30 ml of sterilized water, and were then dispersed and suspended for 10 minutes by a magnetic stirrer. After leaving the resultant mixture standstill, 10 ml of its supernatant was collected and inoculated to 100 ml of an isolating culture medium having the below-described composition and contained in a 500-ml Sakaguchi flask. The contents were shaken and cultured at 30° C. and 120 strokes/min, and for 7 days. This procedure was repeated to effect four enrichment culturing operations.

| (Composition of Separating Liquid Culture Medium) | |
|---|---|
| n-Hexadecane | 100 ml |
| Ammonium nitrate | 25 g |
| Potassium dihydrogenphosphate | 10 g |
| Magnesium sulfate heptahydrate | 5.0 g |
| Potassium chloride | 5.0 g |
| Yeast extract | 1.0 g |
| Tap water | 1000 ml |
|  | (pH 4.5) |

(ii) Thereafter, 0.5 ml of cultured liquid mixture was collected from the enrichment liquid culture medium in each stage and was uniformly coated with a Conradi's rod to the surface of a separating agar culture medium prepared in a manner which will be described hereinafter. Then, the culture medium was covered with a filter paper impregnated with n-hexadecane, sealed with cellophane adhesive tape, and cultured at 30° C.

(Preparation of Separating Agar Culture Medium)

To the above-described separating liquid culture medium with the n-hexadecane excluded therefrom, agar was added in an amount of 2.5 wt. % based on the liquid culture medium, followed by sterilization of the resultant mixture with steam. The thus-sterilized mixture was poured in equal portions into sterilized Petri dishes under heating, thereby to obtain plate agar culture media.

(iii) Then, a Pt spatula of a colony grown by the above culture was diluted to 100 times with sterilized water. Thereafter, 0.1 ml of the thus-diluted solution was again coated to an agar culture medium having the same composition as the above-mentioned separating culture medium. The agar culture medium was also covered with an n-hexane-impregnated filter paper, thereby culturing the culture medium at 30° C. for 3 days while feeding n-hexadecane thereto. It was confirmed by visual and microscopical observations that the resultant plural colonies were not different from one another. Of the above-described colonies, 10 colonies were then inoculated to a slant agar culture medium of the same composition as the separating agar culture medium and while feeding n-hexadecane from an n-hexadecane-impregnated filter paper, the culture medium was cultured at 30° C. for 3 days. It was again confirmed visually and microscopically that the bacteria on the 10 slant culture media were of the same kind. It was also confirmed that the mycological properties and physiological properties of these 10 microorganisms on their respective culture media were identical. The mycological properties and physiological properties of the microorganism on each culture medium were the same as those described above.

As a result of the above tests, the microorganisms cultured respectively on the ten culture media were all determined to be of the same strain isolated from the natural world.

(iv) Then, a Pt spatula of the microorganism pure-cultured above on the slant culture medium was suspended in a sterilized 10% aqueous solution of glycerin (2 ml) contained in a freezing and storing vial. It was frozen and stored at $-80°$ C. After stored in the frozen state for 3 months, it was defrosted promptly. A Pt spatula of the thus-obtained suspension was subjected to anabiosis on a usual agar culture medium. Then, its mycological properties and physiological properties on the respective culture media were investigated under the same conditions as described above. As a result, no changes were observed compared with its corresponding properties before the freezing.

Furthermore, the above freezing and defrosting were repeated every month five times in total. The mycological properties and physiological properties of the resultant microorganisms on their respective culture media were investigated. No changes were however observed.

REFERENTIAL EXAMPLE 1

(i) To a 5-liter culturing Erlenmeyer flask containing 500 ml of a sterilized seed culture medium (pH 6.2) which contained 5 weight/volume % (hereinafter, represented by w/v %) of glucose and 2 w/v % of corn steep liquor, was inoculated 50 ml of a cultured liquid mixture of *Torulopsis bombicola* KSM-36 which liquid mixture was obtained by culturing the same strain at 30° C. for 48 hours in a 500-ml Sakaguchi flask containing a culture medium of the same composition as that contained in the Erlenmeyer flask. The seed culture medium was cultured with shaking at 30° C. for 48 hours. Three hundred milliliters of the thus-cultured liquid mixture were then inoculated to a 30-liter jar fermentor containing 15 liters of a main culture medium (pH 5.6) which contained 15 w/v % of palm oil, 10 w/v % of glucose and 0.5 w/v % of yeast extract and were then cultured for 5 days under the conditions of a temperature of 30° C., aeration of 0.5 VVM, internal pressure of 0.75 kg/cm$^2$, and agitation of 350 rpm.

(ii) About 15 liters of the thus-cultured liquid mixture were placed in a phase-separating tube having an internal diameter of 15 cm and length of 100 cm, which was conical at a free end thereof and equipped with a heating jacket. While stirring the liquid mixture by bubbling air from a lower part of the tube, the liquid mixture was heated at about 70° C. for 30 minutes and the aeration was stopped. The cultured liquid mixture was then allowed to stand for 30 minutes to undergo sedimentation. Here, the cultured liquid mixture separated into four phases. After gently drawing out the lowermost sedimentation phase and a microorganism phase, which lay over the lowermost phase, through a lower nozzle, a water layer which was the next upper phase (i.e., the second phase from the top after the phase separation) was collected gently.

(iii) Thereafter, one liter of the thus-collected water phase was separated and then subjected to extraction with 500 ml of a 2:1 mixed solvent of chloroform and methanol as needed, thereby removing materials, which were soluble in the mixed solvent of chloroform and methanol, from the water phase. After the extraction treatment, the resultant water phase was centrifuged at 5° C. and 3500 rpm and for 30 minutes to obtain a supernatant. Using a rotary evaporator, this supernatant was heated over an oil bath of 35° C. to distill off the mixed ethanol and the like and at the same time to concentrate it under reduced pressure. In order to remove ionic materials from about 50 ml of the thus-obtained liquid concentrate, both cation-exchange resin and anion-exchange resin were added to the liquid concentrate. After stirring the mixture for 2 hours, the ion-exchange resins were washed and removed.

(iv) Then, 320 ml of the thus-deionized water layer was charged in its entirety in an activated carbon column. As the activated carbon column, was used that obtained by packing 180 ml of activated carbon [activated carbon for chromatography; product of Wako Pure Chemicals Co., Ltd.] in a glass column having an inner diameter of 2.5 cm and a length of 60 cm, causing 1000 ml of an aqueous 4N-HCl solution to flow through the thus-packed glass column, and then causing 4000 ml of distilled water to flow through the glass column. The isolation operation making use of the activated carbon column was completed by effecting stepwise elution, namely, causing firstly 1000 ml of distilled water, and thereafter, 2500 ml of a 5% aqueous solution of ethanol, 1000 ml of a 10% aqueous solution of ethanol and 1000 ml of a 20% aqueous solution of ethanol to flow as eluents in order, and finally by causing 1000 ml of a 50% aqueous solution of ethanol. The eluates were separately collected at 100 g/fraction by a large fraction collector. The thus-separated fractions were each analyzed by thin-layer chromatography, gas chromatography, gas chromatography-mass spectrometry (GC-MS) and the like. As a result, the material separated into the fraction No. 11 to fraction No. 40 was confirmed to be sophorose (The sole FIGURE). Under the above fermentation conditions, sophorose was obtained in an amount of about 30 g per liter of the liquid fermentation mixture. It was also confirmed that the fraction No. 1 to fraction No. 10 contained mannitol. Mannitol was obtained in an amount of about 12 g per liter of the liquid fermentation mixture.

What is claimed is:

1. A biologically pure culture of *Torulopsis bombicola* KSM-36 (FRI Deposition FERM BP-799) having the following mycological properties:
   (a) state of growth on various culture media: grows into elliptical to elongated elliptical Yeasts having a size of (0.75 to 3.0)×(1.5 to 5.5) μm on malt culture medium, malt agar, potato dextrose agar, and corn meal agar, and no formation of euhyphae or pseudohyphae is observed by the multipolar budding type;
   (b) formation of ascospores: using malt extract agar, no formation of ascosporres is observed;
   (c) formation of ballistosxpores: culturing on malt agar, no formation of ballistospores is observed;

(d) various physiological properties:
   (1) growth conditions:
      pH: 3 to 8 (optimum pH: 5 to 6)
      temperature: 7 to 38° C. (optimum temperature: 25 to 34° C.)
   (2) assimilation of salts of nitric acid: (−)
   (3) decomposition of fat: (+)
   (4) liquefaction of gelatin: (−)
   (6) resistance to sodium chloride: 6–8% (w/v)
   (7) formation of carotenoid pigments: (−)
   (8) formation of organic acids in Caster's culture medium: (+)
   (9) formation of starch-like substances: (−)
   (10) vitamin requirement: (+)

(e) assimilating capacity and fermenting capacity:

|  | assimilating capacity | fermenting capacity |
| --- | --- | --- |
| (1) D-glucose | (+) | (+) |
| (2) trehalose | (−) | (−) |
| (3) D-galactose | (−) | (−) |
| (4) lactose | (−) | (−) |
| (5) sucrose | (+) | (+) |
| (6) raffinose | (−) | (+½) |
| (7) D-mannose | (−) | (−) |
| (8) D-xylose | (−) |  |
| (9) α-methyl-D-glucoside | (−) |  |
| (10) melibiose | (−) |  |
| (11) D-arabinose | (−) |  |
| (12) esculin | (−) |  |
| (13) ethanol | (+) |  |
| (14) inositol | (−) |  |
| (15) maltose | (−) | (−) |
| (16) melezitose | (−) |  |
| (17) glycerin | (+) |  |
| (18) cellobiose | (−) |  |
| (19) inulin | (−) |  |
| (20) D-mannitol | (+) |  |
| (21) soluble starch | (−) |  |
| (22) D-sorbitol | (+) |  | and,
(f) productivity of sophorose:
   high sophorose producing activity.

* * * * *